US006605667B1

(12) United States Patent
Badejo et al.

(10) Patent No.: US 6,605,667 B1
(45) Date of Patent: Aug. 12, 2003

(54) ANTIOXIDANT ENRICHED ADHESIVE COMPOSITIONS AND STORAGE CONTAINERS THEREFOR

(75) Inventors: Ibraheem T. Badejo, Morrisville, NC (US); Jaime Ayarza, Raleigh, NC (US); Anthony Voiers, Raleigh, NC (US); Roy F. Thompson, Jr., Wake Forest, NC (US); Gabriel N. Szabo, Raleigh, NC (US); Robert V. Toni, Raleigh, NC (US); William S. C. Nicholson, Durham, NC (US)

(73) Assignee: Closure Medical Corporation, Raleigh, NC (US)

( * ) Notice: Subject to any disclaimer, the term of this patent is extended or adjusted under 35 U.S.C. 154(b) by 164 days.

(21) Appl. No.: 09/657,913

(22) Filed: Sep. 8, 2000

(51) Int. Cl.⁷ .................................................. C08K 5/15
(52) U.S. Cl. ...................... 524/753; 524/751; 526/310; 526/328; 424/443; 424/447; 424/448
(58) Field of Search ................................ 526/310, 328; 524/751, 753; 424/443, 447, 448

(56) References Cited

U.S. PATENT DOCUMENTS

| | | |
|---|---|---|
| 2,721,858 A | 10/1955 | Joyner et al. |
| 3,254,111 A | 5/1966 | Hawkins et al. |
| 3,559,652 A | 2/1971 | Banitt et al. |
| 3,940,362 A | 2/1976 | Overhults |
| 3,995,641 A | 12/1976 | Kronenthal et al. |
| 4,125,494 A | 11/1978 | Schoenberg et al. |
| 4,139,693 A * | 2/1979 | Schoenberg ............... 526/297 |
| 4,313,865 A | 2/1982 | Teramoto et al. |
| 4,321,180 A | 3/1982 | Kimura et al. |
| 4,364,876 A | 12/1982 | Kimura et al. |
| 4,560,723 A | 12/1985 | Millet et al. |
| 4,720,573 A | 1/1988 | Lin |
| 4,724,111 A | 2/1988 | Iwata et al. |
| 5,034,456 A | 7/1991 | Katsumura et al. |
| 5,328,687 A | 7/1994 | Leung et al. |
| 5,462,536 A * | 10/1995 | Braatz et al. ............... 604/304 |
| 5,514,371 A | 5/1996 | Leung et al. |
| 5,514,372 A | 5/1996 | Leung et al. |
| 5,525,647 A | 6/1996 | Eichmiller |
| 5,530,037 A | 6/1996 | McDonnell et al. |
| 5,534,561 A * | 7/1996 | Volke ......................... 523/111 |
| 5,575,997 A | 11/1996 | Leung et al. |
| 5,582,834 A | 12/1996 | Leung et al. |
| 5,624,669 A | 4/1997 | Leung et al. |
| 5,691,016 A | 11/1997 | Hobbs |
| 5,770,135 A | 6/1998 | Hobbs et al. |
| 5,811,446 A * | 9/1998 | Thomas ....................... 514/399 |
| 5,866,106 A | 2/1999 | Papay |
| 5,928,611 A | 7/1999 | Leung |
| 6,238,692 B1 * | 5/2001 | Smith ........................ 424/448 |

FOREIGN PATENT DOCUMENTS

| | | |
|---|---|---|
| EP | 0 659 441 A1 | 6/1995 |
| GB | 2 107 328 A | 10/1981 |
| JP | 54 036642 B | 11/1979 |
| JP | A-64-20206 | 1/1989 |
| JP | A-5-145777 | 6/1993 |
| JP | 10 328291 A | 12/1998 |
| WO | WO 99/42142 | 8/1999 |

* cited by examiner

*Primary Examiner*—Helen L. Pezzuto
(74) *Attorney, Agent, or Firm*—Oliff & Berridge, PLC

(57) ABSTRACT

An adhesive composition includes a polymerizable adhesive monomer and at least one antioxidant stabilizer, and/or a container for storing said monomer composition that includes an antioxidant stabilizer. The antioxidant stabilizer provides superior stabilization and shelf-life of the composition and/or the container, and may enhance wound healing properties of the monomer composition.

76 Claims, No Drawings

ANTIOXIDANT ENRICHED ADHESIVE COMPOSITIONS AND STORAGE CONTAINERS THEREFOR

BACKGROUND OF THE INVENTION

1. Field of Invention

The present invention relates to monomer and polymer adhesive and sealant compositions, and to their production and use for industrial and medical applications. In particular, the present invention relates to the incorporation of antioxidant stabilizers in adhesive compositions, such as during manufacture (e.g., sterilization processing), shipment and/or storage, and/or storage containers for such compositions to stabilize the compositions and/or the storage containers, and potentially to enhance the wound healing properties of such compositions when used for medical purposes.

2. Description of Related Art

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal (including human) tissue. Monomers of α-cyanoacrylates are anionically polymerizable or free radical polymerizable, or polymerizable by zwitterions or ion pairs to form polymers. Once polymerization has been initiated, the cure rate can be very rapid.

Medical applications of 1,1-disubstituted ethylene adhesive compositions include use as an alternate or an adjunct to surgical sutures and/or staples in wound closure, as well as for covering and protecting surface wounds such as lacerations, abrasions, burns, stomatitis, sores, minor cuts and scrapes, and other wounds. When an adhesive is applied to surfaces to be joined, it is usually applied in its monomeric form, and the resultant polymerization gives rise to the desired adhesive bond.

The industrial production of 1,1-disubstituted ethylene monomer adhesive compositions has been optimized to provide adhesives with rapid cure rates and high bond strengths. However, the desire to provide an adhesive with a rapid cure rate has led to problems with shelf-life. The shelf-life of these adhesives is primarily related to stability (i.e., constancy of compositional nature), uncured physical properties, rate of cure of the adhesive, as well as final cured properties of the composition. For example, the shelf-life of a monomeric α-cyanoacrylate composition is related to the amount of time the composition can be stored before unacceptable levels of polymerization occur. Unacceptable levels are indicated by a level of polymerization product that reduces the usefulness of the composition in the application for which it is produced. It is well known that monomeric forms of α-cyanoacrylates polymerize rapidly in the presence of even minute amounts of an initiator, and that once polymerization has been initiated, the rate of cure can be very rapid. Therefore, in order to obtain a monomeric α-cyanoacrylate composition with an extended shelf-life, polymerization inhibitors such as anionic and free radical stabilizers are often added to the compositions. However, addition of such stabilizers can result in substantial retardation of the cure rate of the composition. Therefore, in the production of industrial α-cyanoacrylate adhesives, the amount of stabilizers added is minimized so that the cure rate is not adversely affected.

Cyanoacrylate adhesives used in medical applications preferably have a shelf-life of at least twelve months. In order to achieve a useful shelf-life, anionic and free-radical stabilizers are generally added to the monomer compositions.

As disclosed in U.S. Pat. Nos. 3,559,652 to Banitt et al. and 5,582,834 to Leung et al., for example, suitable stabilizers for medically useful α-cyanoacrylate compositions include Lewis acids such as sulfur dioxide, nitric oxide, and boron trifluoride, as well as free-radical stabilizers including hydroquinone, monomethyl ether hydroquinone, nitrohydroquinone, catechol, and monoethyl ether hydroquinone. The combination of the two anionic stabilizers sulfur dioxide and sulfonic acid is also known and is disclosed in, for example, British Patent Application GB 2 107 328 A. However, the use of these two anionic stabilizers in combination does not overcome the "speed loss" seen in other 1,1-disubstituted ethylene adhesive compositions.

In addition to having an extended shelf-life, cyanoacrylate compositions for use in many medical applications should be sterile. Due to the importance of achieving and maintaining sterility of these compositions, when an additive, such as an anionic or free-radical stabilizer, is added to an α-cyanoacrylate composition, it should be added prior to sterilization. However, regardless of the type and number of additives, sterilization of α-cyanoacrylate adhesive compositions is often difficult to achieve. For example, widely practiced methods of sterilization, such as heat sterilization and ionizing radiation, are often not suitable for use with monomeric cyanoacrylate compositions. Problems arise due to polymerization of the monomer during the sterilization process, even in the presence of stabilizers. In many cases, sterilization-induced polymerization is so severe that the resulting product is unusable. Furthermore, even when the sterilized product is still useable, the shelf-life at desired storage temperatures, such as under refrigerated conditions or at room temperature, can be shortened to such a degree that the product is not suitable for commercialization.

Methods currently used to package and sterilize α-cyanoacrylate monomer compositions have been developed with the recognition that, to improve efficiency and productivity, the packaging and sterilizing steps should be performed in rapid succession. However, these methods do not provide the desired shelf-life of the adhesive compositions in all packaging materials.

Furthermore, during sterilization, much or all of the stabilizer can be consumed or converted to another compound. For example, U.S. Pat. No. 5,530,037 to McDonnell et al. discloses that when a low level of sulfur dioxide is used to stabilize a cyanoacrylate composition, all of the sulfur dioxide is converted to sulfuric acid during the sterilization process. Thus, although polymerization during sterilization can be minimized by use of low levels of sulfur dioxide, and shelf-life of the sterilized α-cyanoacrylate adhesive composition can be increased, shelf-life might be improved by the presence of increased amounts of sulfur dioxide in the initial composition. Unfortunately, at initial high levels of a stabilizer, the general performance of the adhesive can be impaired and the shelf life provided still is less than desired.

McDonnell et al. also teaches that the use of the free radical stabilizers butylated hydroxyanisole (BHA) and butylated hydroxytoluene (BHT), in combination with 100 parts per million (final concentration) sulfur dioxide, are not effective at stabilizing α-cyanoacrylate compositions during gamma irradiation sterilization. Rather, they must be present in concentrations substantially above 1000 parts per million or higher in order to provide effective stabilization.

In addition, various phenolic stabilizers have been used for stabilizing adhesive compositions. For instance, McDonnell et al. teaches the use of a free radical stabilizer selected from phenolic antioxidants (except for hydroquinone). U.S. Pat. No. 4,125,494 to Schoenberg teaches the use of anionic inhibitors including phenolic compounds such as hydroquinone, t-butyl catechol, pyrocatechol, p-methoxyphenol, and the like. U.S. Pat. No. 4,724,177 to Russo teaches the use of free radical stabilizers including hydroquinone, monomethylether hydroquinone, nitrohydroquinone, and hydroquinone monoethylether. U.S. Pat. No. 5,034,456 to Katsumura teaches the use of radical polymerization inhibitors including hydroquinone, hydroquinone monomethyl ether, catechol, pyrogallol and the like. U.S. Pat. No. 4,321,180 to Kimura teaches the use of radical polymerization inhibitors such as aryl alcohols, phenol, cresols, hydroquinone, benzoquinone, α-naphthol, β-naphthol, catechol, pyrogallol, bisphenol-A, bisphenol-S, 2,6-di-tert-butylphenol, 2,6-di-tert-butylcresol, 2,2'-methylene-bis(4-methyl-6-tert-butylphenol), 4,4'-butylidene-bis(3-methyl-6-tert-butylphenol), 4,4'-thiobis(3-methyl-6-tert-butylphenol), hydroquinone monomethyl ether, 2-hydroxybenzophenone, phenylsalicylic acid, 1,3,5-trimethyl-2,4,6-tris(3,5-di-tert-butyl-4-hydroxybenzyl) benzene and the like.

In addition to the need to stabilize cyanoacrylate adhesive compositions to prevent them from prematurely polymerizing, there is also a need for more robust packaging to prevent premature polymerization of stored adhesive compositions.

Because of the extreme reactivity of monomeric forms of α-cyanoacrylates, a concern in the storage and distribution of these adhesive compositions is the ability to package these adhesives to maximize product shelf-life. It has been found that these monomers show a high degree of transmission into and through polymeric materials commonly used in containers. When these α-cyanoacrylate monomers pass through the container walls and reach the exterior surface of the container, they can polymerize and/or crystallize, generally forming a white, powdery material on the exterior surface of the container. This polymerization and/or crystallization is often referred to as "blooming" and is an indicator of failure of the container material. In addition, monomers that enter into the polymeric matrix of the container can polymerize within the matrix before reaching the other side of the matrix and cause the container to fail, such as through swelling, cracking, splitting, or otherwise weakening of the polymeric matrix. Furthermore, monomers can interact with the polymer matrix, similarly resulting in failure of the container material. Because of these problems and the potential for premature polymerization of the monomer during storage, it is important to package the monomer in a container that is highly resistant to attack, salvation, and/or permeation by 1,1-disubstituted ethylene monomer compositions.

Containers made of polymeric materials are well known in the art. For example, containers made of polyoelefins, such as polyethylene (PE), polypropylene (PP), polystyrene, polyvinylchloride (PVC), and thermoplastic elastomer are widely used. Similarly, fluorocarbons such as Halar® ethylene-chlorotrifluoroethylene copoloymer (ECTFE) (Allied Chemical Corporation, Morristown, N.J.), Tefzel® ethylene-tetrafluoroethylene (EFTE) (E.I. duPont de Nemours and Co., Wilmington, Del.), tetrafluoroethylene (TFE), polytetrafluoroethylene (PTFE), polytetrafluoroethylene fluorinated ethylenepropylene (PTFE-FEP), polytetrafluoroethylene perfluoroalkoxy (PTFE-PFA), and polyvinylidene fluoride (PVDF) are used as container materials. Further, engineered resins, such as polyamide (e.g. nylon), polyphenylene oxides, and polysulfone, are also used as container materials.

In choosing a suitable container for a particular application, its chemical and physical properties in relationship to the properties of its contents as well as its cost are among the primary considerations. The polymeric material used to form the container must be essentially inert with respect to the composition to be contained during the period in which the composition is contained. That is, the polymeric material used to form the container must not substantially react with or catalyze reaction of the material contained in the container, preferably over at least an intended life (or shelf-life) of the material. The polymeric material must also provide adequate physical containment and protection during the period in which the composition is contained. For example, in biological research settings, containers are often selected for their ability to stably contain aqueous compositions intended for culturing of microorganisms. In chemical and industrial settings, containers that show high resistance to attack and/or degradation by chemicals, such as acids, bases, solvents, and organics, are widely used. Likewise, in medical applications, containers that exhibit resistance to irradiation, such as gamma or electron-beam irradiation, are also used.

For example, U.S. Pat. Nos. 5,691,016 and 5,770,135 to Hobbs et al. disclose containers that are resistant to permeation by hydrocarbon fuels, and methods for producing these containers. The patents disclose a process for producing fluorinated plastic containers with excellent resistance to permeation by hydrocarbon fuels. The process relies on blow-molding of plastic containers in the presence of fluorine-containing gases. In the process, a parison is formed from the pre-heated thermoplastic material, expanded within a closed mold by means of an inflating gas, and subjected to multiple fluorination treatment steps to affect fluorination of the interior surface of the parison. The containers made by such processes exhibit resistance to permeation by hydrocarbon fuels, such as motor oil.

Furthermore, it was known to form containers from materials that provide barrier properties. Fluoropolymers are known for such use. For example, U.S. Pat. No. 5,016,784 to Batson discloses an applicator syringe for containing and dispensing moisture-sensitive adhesive. The syringe comprises a generally sealed barrel containing a plunger having a non-stick polymeric seal and a hydrocarbon grease disposed between the seal and the adhesive contained in the barrel. The barrel is made of non-reactive fluoropolymer such as poly(monochlorotrifluoroethylene). The non-stick polymeric seal is also made of a fluoropolymer selected from polytetrafluoroethylene, polychlorotrifluoroethylene, fluorinated ethylene propylene polymers, and polyvinylidene fluoride. The moisture sensitive adhesive is generally described as a cyanoacrylate adhesive.

Also, the use of various additives to stabilize storage vessels is known. For instance, U.S. Pat. No. 5,525,647 to Eichmiller teaches a storage container treated with butylated hydroxytoluene (BHT). Japanese Patent No. 1-20206 to Kuboshima teaches a container for quick setting adhesives, wherein the container includes phenolic antioxidants. In addition, Japanese Patent No. 5-145777 to Sakabe teaches a plastic container for storing adhesives, wherein an inner container contains the adhesive material and the inner container is placed in an outer container that includes a deoxygenating agent including FeO, FeOH and the like.

Adhesives can comprise either organic or inorganic compounds, or a combination of the two, and have broad utility in both industrial (including household) and medical applications. Because it is most economical for manufacturers to produce adhesives on a large scale, and for merchants to purchase adhesives in bulk quantities prior to sale to consumers, adhesives are often stored for extended periods of time between manufacture and use. Therefore, they must be stored in containers that are capable of maintaining them in a substantially unadulterated state for a reasonable amount of time in order to make their bulk manufacture and purchase economical. Reasonable storage times apply to containers holding large volumes (such as greater than one liter), which are typically purchased by industrial concerns, as well as those holding small volumes (such as one liter or less, even a few milliliters, such as 10 milliliters, or less), which are typically purchased by medical and individual consumers.

In addition to the widespread use of adhesives in industrial applications, recently the medical profession (including veterinary medicine) has begun to use certain adhesives as replacements for, or adjuncts to, sutures and staples for closure of wounds, as biological sealants, and as wound coverings. Among the adhesives currently being used for medical purposes are adhesives formed from 1,1 - disubstituted ethylene monomers, such as the α-cyanoacrylates. Typically, for medical purposes, an adhesive should have a shelf-life of at least one year; however, an increased shelf-life beyond this provides increased economic advantages to both the manufacturer and the consumer. As used herein, "shelf-life" refers to the amount of time the container and composition therein can be held at a desired temperature, such as under refrigerated conditions, at room temperature (i.e., about 21–25° C.), or the like without degradation of the composition and/or container occurring to the extent that the composition and container cannot be used in the manner and for the purpose for which they were intended. Thus, while some degradation to either or both of the composition and container can occur, it must not be to such an extent that the composition and/or container is no longer useable. Shelf-life can thus be limited by physical or aesthetic changes to the containers or products contained therein, by chemical reactions occurring within the composition being stored, by chemical reactions between the container and the composition being stored, by degradation of the container itself, and the like.

Because the α-cyanoacrylates have become the most widely used adhesives for medical applications, containers that can hold these adhesives for extended periods of time without loss of the expected qualities of the adhesive (adherence, cure time, biological safety, purity, etc.) are essential.

Thus, a need exists not only for improved monomer cyanoacrylate adhesive compositions, for both industrial and medical uses, having a longer shelf-life without sacrificing the performance of the adhesive, but also for more robust packaging that can extend the shelf-life of stored cyanoacrylate adhesive compositions.

SUMMARY OF THE INVENTION

The present invention provides an improved monomeric adhesive composition and/or an improved adhesive composition storage container, wherein the adhesive composition and/or the container comprise a selected antioxidant stabilizer.

The present invention provides a monomer-containing adhesive composition comprising a polymerizable 1,1-disubstituted ethylene monomer, such as α-cyanoacrylate monomer, and at least one selected antioxidant. As used herein, an "antioxidant" means a compound that prevents degradation caused by oxidation.

The combination of a polymerizable monomer with at least one selected antioxidant according to the present invention provides an adhesive monomer composition with an enhanced and extended shelf-life and enhanced wound healing properties as compared to similar compositions lacking such antioxidants. The present invention also provides an adhesive monomer composition with an enhanced and improved ability to withstand sterilization processing, such as gamma or electron beam irradiation processing, as compared to similar compositions lacking such antioxidants. As used herein "extended shelf-life" refers to a shelf-life of at least 12 months, preferably at least 18 months, and even more preferably at least 30 months. Moreover, "enhanced wound healing capabilities" as used herein refers to the well known ability of antioxidants to reduce free radicals that may otherwise hinder the ability of a wound to heal. Although it is known to add polymerization inhibitors (stabilizers) to monomeric adhesive compositions, the superiority of the use of an antioxidant stabilizer according to the present invention, to provide added stability and/or to enhance wound healing, has not been previously recognized.

The present invention also provides containers (including storage vessels, dispensers, applicators, and the like) comprising antioxidant enriched polymeric materials that provide an extended shelf-life for 1,1-disubstituted ethylene monomers for both industrial and medical uses. Containers of the present invention comprise a selected antioxidant that renders the container highly resistant to the effects of permeation by liquids and gases (including vapors, such as water vapor, that act as polymerization initiators), as well as highly resistant to degradation by 1,1-disubstituted ethylene monomers. As used herein "degradation" of the container includes, but is not limited to, chemical attack, swelling, cracking, etching, embrittlement, solvation, and the like. The containers further provide resistance to degradation of the 1,1-disubstituted ethylene monomers contained therein. As used herein, "degradation" of the composition includes, but is not limited to, premature polymerization (as reflected by viscosity changes) and undesirable changes in reactivity (including increases or decreases in cure time).

The present invention also includes a process for enhancing the wound healing properties of such adhesive compositions, and for increasing the shelf-life of such adhesive compositions. The enhancement of the wound healing properties of the compositions includes combining the monomer with a selected antioxidant stabilizer, either by itself or in combination with a non-antioxidant medicament. In addition, the process of extending the shelf-life of the composition similarly includes combining the monomer with a selected antioxidant stabilizer and/or adding a selected antioxidant to at least an interior surface of the container post-fabrication, or to a bulk material of the container before or during fabrication.

DETAILED DESCRIPTION OF EMBODIMENTS

According to the present invention, a stable monomeric adhesive composition is manufactured by combining at least one antioxidant stabilizer with a composition comprising a monomer adhesive. The at least one antioxidant stabilizer according to the present invention 1) may inhibit polymerization of the monomer of the composition to a greater extent than can be achieved in prior art compositions, particularly during sterilization processing, and/or 2) may enhance the wound healing properties of the adhesive when used in medical applications.

The antioxidant stabilizer can be selected from among known antioxidants, including, but not limited to, vitamin E ($C_{29}H_{50}O_2$) (including alpha-tocopherol ($C_{29}H_{50}O_2$), beta-tocopherol ($C_{28}H_{48}O_2$), gamma-tocopherol ($C_{28}H_{48}O_2$) and delta-tocopherol ($C_{27}H_{46}O_2$) and derivatives thereof, vitamin K (including phylloquinone ($C_{31}H_{46}O_2$), menaquinone (e.g. menaquinone 4 ($C_{31}H_{40}O_2$)), and menadione ($C_{11}H_8O_2$) and derivatives thereof, including but not limited to vitamin $K_1$ chromanol and vitamin $K_1$ chromenol, vitamin C (ascorbic acid ($C_6H_8O_6$)) and derivatives thereof, pentamethyl chromanol ($C_{14}H_{20}O_2$), non-phenolic antioxidants, octyl gallate ($C_{14}H_{20}O_5$) and pentamethyl benzofuranol ($C_{13}H_{18}O_2$). A preferred vitamin E antioxidant is any of the series of IRGANOX® brand vitamin E (available from Ciba Specialty Chemical Co.). A preferred pentamethyl chromanol is 2,2,5,7,8-pentamethyl-6-chromanol. Representative chemical structures of the above-listed antioxidant stabilizers are depicted below. Derivatives of the described compounds, particularly where the moieties are benzopyranols or benzofuranols, are also suitable.

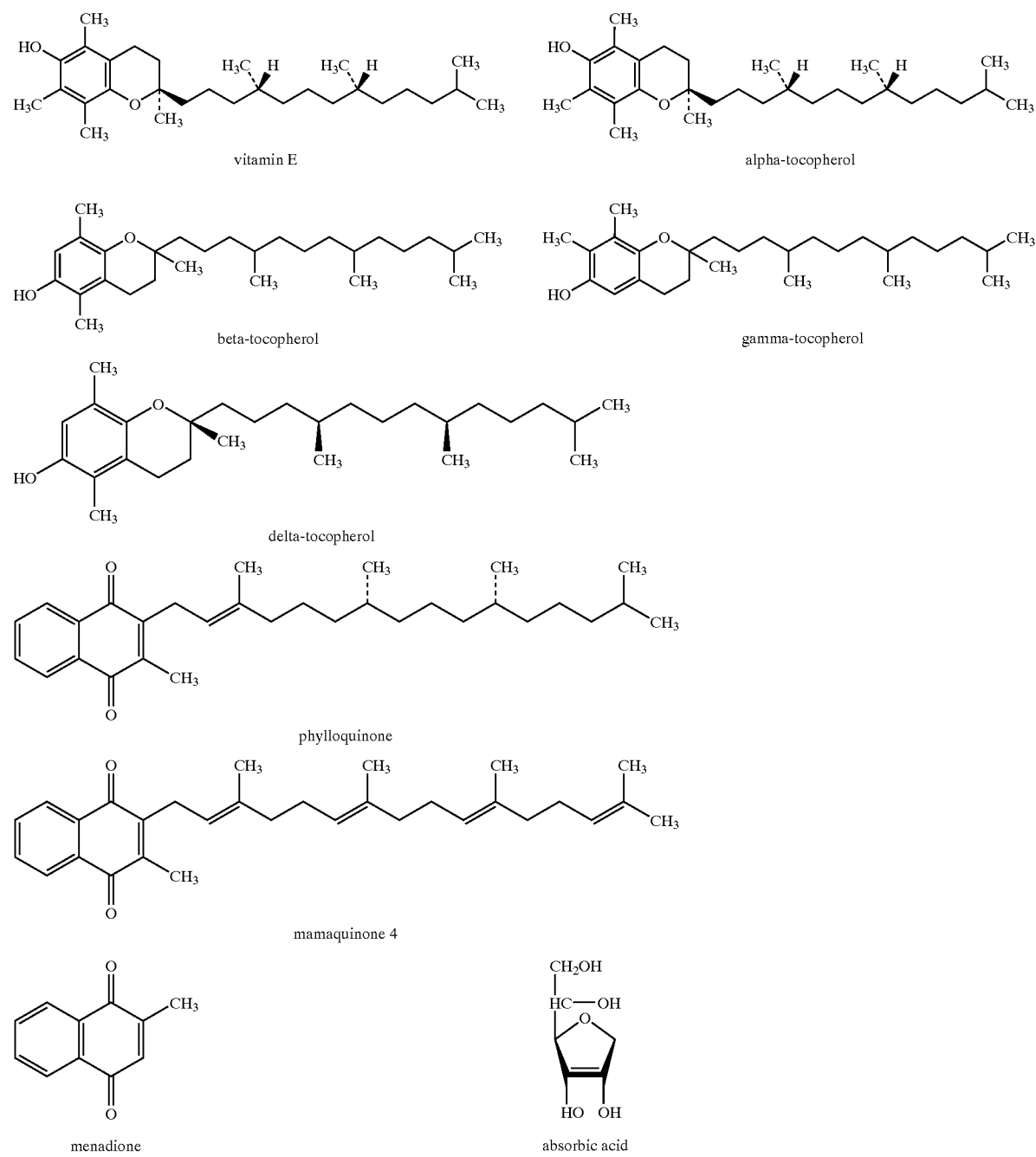

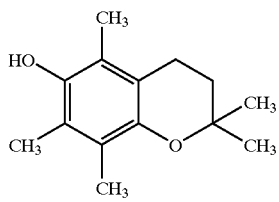

pentamethyl chromanol

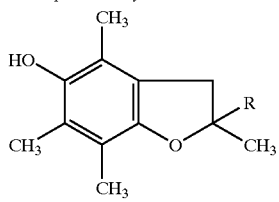

pentamethyl benzofuranol

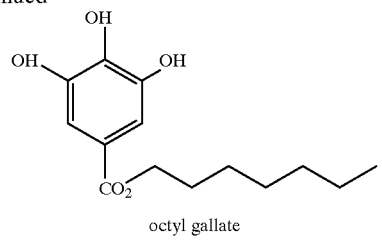

octyl gallate

Other suitable antioxidant stabilizers include compounds of the following formula:

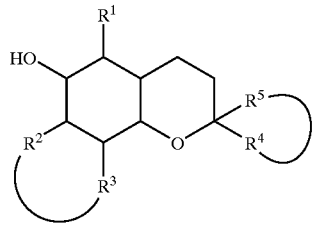

where $R^1$, $R^2$, $R^3$, $R^4$, and $R^5$ are independently selected from hydrogen, substituted alkyl or unsubstituted alkyl groups having from, for example, 1 to about 20 carbon atoms. Furthermore, suitable compounds include those of the above formula where $R^2$ and $R^3$, and/or $R^4$ and $R^5$, may optionally form cyclic groups having from about 2 to about 40 carbon atoms, preferably from about 2 or about 3 to about 6 or about 8 carbon atoms.

In embodiments, various suitable non-phenolic antioxidants can be used. By "non phenolic antioxidants" are meant those antioxidants that may or may not have a benzene ring or other cyclic structure, but which do not have a phenol structure per se. Thus, for example, suitable non phenolic antioxidants include, but are not limited to, chromanols, such as pentamethyl chromanol, benzopyranols, benzofuranols such as pentamethyl benzofuranol, and the like.

The amount of antioxidant stabilizer that is added to the monomer composition depends on the monomer to be stabilized, the stabilizer being selected, and/or the packaging material to be used for the composition. Preferably, an antioxidant selected from vitamin E and its derivatives, vitamin K and its derivatives and vitamin C and its derivatives is added in an amount of at least 0.1 percent, preferably more than 0.1 percent or at least 0.2 percent by weight based on the monomer. Although adding the above antioxidants in an amount equal to at least 0.1 percent or at least 0.2 percent by weight is suitable, in other embodiments, such antioxidants are preferably added in an amount of at least about 0.3 percent by weight, or at least about 0.4 percent by weight, and up to about 1 or 2 percent by weight, based on a total weight of the monomer. Of course, higher amounts of the antioxidant can be added, as desired. Preferably, the vitamin antioxidants are contained in the monomer composition in an amount of from about 0.1 percent or about 0.2 to about 2.0 percent by weight, for example from about 0.3 to about 1.0 percent by weight or from about 0.4 to about 0.7 percent by weight, and such as about 0.5 percent by weight, based on a total weight of the monomer.

Preferably, according to the present invention, the antioxidant stabilizer is included in the composition in an amount not only to provide effective stabilization of the monomeric adhesive composition, but also to provide wound healing properties to the composition. Thus, for example, the antioxidant stabilizer is included in an amount that provides sufficient residual antioxidant stabilizer in a formed polymeric material, such that the antioxidant can diffuse out of the formed polymer over time. By such diffusion, the antioxidant stabilizer is made available to an adjacent tissue and/or a surrounding environment to impart wound healing properties.

As used herein an amount of stabilizer sufficient or effective "to stabilize" the monomer composition refers to the an amount of stabilizer sufficient to prevent the viscosity of a sterilized monomer composition from increasing to more than 200%, and preferably 150%, of the composition's initial viscosity after sterilization. Suitable monomer composition stability, in terms of composition viscosity, according to the present invention is disclosed in U.S. patent application Ser. No. 09/374,207 filed Aug. 12, 1999, the entire disclosure of which is incorporated herein by reference.

Also, other suitable antioxidants, including but not limited to, pentamethyl chromanol, non-phenolic antioxidants, octyl gallate and pentamethylbenozofuranol can be added in amounts of from about 0.01 to about 10 percent or more, preferably up to about 5 percent or more or 2.0 percent or more by weight based on the monomer. In preferred embodiments, such antioxidant stabilizers are present in an amount from about 0.05 to about 5 percent or about 1.0 percent by weight based on the monomer, for example from about 0.1 to about 1.0 percent by weight based on the monomer, or from about 0.2 or 0.3 to about 0.7 or 0.8 percent by weight based on the monomer, and such as about 0.5 percent by weight based on the monomer. Contents outside of these ranges can be used, in embodiments, as desired. Thus, for example, where the antioxidants stabilizer is a higher molecular weight compound, greater amounts of the antioxidant can be used to obtain the desired result.

In embodiments of the present invention, the antioxidant is included in the composition in an amount effective to provide effective stabilization of the composition. Thus, for example, the antioxidant is contained in an amount effective to stabilize the composition over a desired shelf-life of the product, and/or to stabilize the composition during and after any applicable sterilization procedure. A particular advantage of the antioxidant stabilizers is that they provide effective stabilization of the composition during sterilization procedures, such as irradiation, dry heat, and/or chemical sterilization processes. Accordingly, and as necessary, the amount of the antioxidant added to the composition can be varied depending upon, for example, the projected shelf-life of the composition and/or the kind and degree of selected sterilization processing. Such selection and variation of the antioxidant can be performed by one of ordinary skill in the art with only routine experimentation.

In addition, in embodiments of the present invention an antioxidant stabilizer may be added in amounts to further stabilize the composition upon exposure to light, such as fluorescent light, incandescent light, and the like. Suitable stabilizers include, but are not limited to, the above listed antioxidant stabilizers. It has been found that incorporation of such antioxidant stabilizers into the polymerizable composition provides the composition with a greater stability (i.e., longer shelf-life) when exposed to such light sources as compared to similar compositions not including the antioxidant stabilizers In embodiments of the present invention, particularly where the composition is to be used as a wound dressing or is otherwise being applied to tissue, the antioxidant can be included in the composition for its wound healing properties as well as for its stabilization properties. In these embodiments, if desired, the amount of the stabilizer contained in the composition can be increased, so that an effective amount of the stabilizer remains present in the resultant polymer. When so present, the antioxidant is generally released or diffuses from the polymer, either immediately or over time, into the tissue. Accordingly, one or more of the above-described antioxidants can be included in the composition for their wound-healing effects.

In addition, according to the present invention, antioxidant stabilizer can, additionally or alternatively, be included in a container that is used to contain polymerizable monomer adhesive compositions, such as 1,1-disubstituted adhesive compositions and cyanoacrylate adhesive compositions. When antioxidant is included in the container material, the resultant container provides increased shelf-life to the contained adhesive composition, whether the contained adhesive composition is a conventional adhesive composition, or an adhesive composition of the present invention that also contains an antioxidant stabilizer.

In particular, the inventors discovered that providing an antioxidant stabilizer in at least the monomer-contacting surfaces (i.e. interior surfaces) of the container, and/or the container cap and/or nozzle and/or other components if present, provides an unexpectedly superior shelf-life, especially for 1,1-disubstituted ethylene monomers, including, but not limited to cyanoacrylates such as lower and higher alkyl chain length alkyl α-cyanoacrylate adhesive monomer compositions. Thus, the present invention provides a container that is more stable than comparable containers not including the antioxidant. That is, the containers of the present invention more effectively prevent radicals from entering into the contained composition through the container walls, which radicals may tend to destabilize the container and/or the composition contained within the container. The containers of the present invention are thus better for containing low molecular weight monomers, including 1,1-disubstituted ethylene monomers such as α-cyanoacrylate monomers, and are economical to manufacture. In addition, in embodiments where the adhesive is to be used for medical purposes, the container is compatible with a broader range of sterilization processes (e.g. gamma irradiation, e-beam irradiation, heat, etc.).

Co-pending U.S. patent application Ser. No. 09/430,289, filed Oct. 29, 1999, the entire disclosure of which is incorporated herein by reference, discloses and claims containers, and methods for producing such containers, where the container is fluorinated, or otherwise treated, to provide increased shelf-life to a contained monomer composition. The principles disclosed in the co-pending application are directly applicable to the present invention, except that the present invention's inclusion of an antioxidant stabilizer in the container material, either in addition to or in place of the halogenated material, provides further advantages to the container in terms of manufacturing, appearance, and the like.

In particular, because processes according to the present invention obtain enhanced stability by the addition of an antioxidant stabilizer, processes of the present invention provide a desirable addition or alternative to fluorinating the container prior to filling it with an adhesive composition to ensure impermeability. By eliminating the need to fluorinate the container, the present invention dramatically reduces the cost of packaging cyanoacrylate adhesive compositions. Furthermore, because the incorporated antioxidant stabilizer eliminates the need to fluorinate the container, an antioxidant enriched container according to the present invention will not exhibit undesirable physical property changes sometimes associated with fluorinated containers (e.g., increased rigidity of fluorinated HDPE containers believed to lead to leaking and other customer/quality issues).

The present invention provides containers that are more highly impermeable to 1,1-disubstituted ethylene monomers, to thereby provide an extended shelf-life to the container and the monomers contained therein. The present invention accomplishes these objectives by providing an antioxidant on at least a surface of the container that comes into contact with the monomer, e.g., the internal surface of the container. In embodiments, this antioxidant is provided by incorporating the antioxidant into or onto the monomer-contacting surfaces, or the interior surfaces, of the container, and/or the container cap and/or nozzle or other components, such as by incorporating the antioxidant into the bulk material of the container during fabrication (e.g., during blow molding of the container). The incorporation of antioxidant stabilizer into or onto the monomer-contacting surfaces of the container is believed to alter the surface the container, by stabilizing the bulk material.

In embodiments, the container comprises any suitable polymeric material, which can be halogenated or non-halogenated, and which is subjected to an incorporated antioxidant that stabilizes at least the monomer-contacting surfaces of the container. This stabilization provides extended shelf-life to the container and to an adhesive composition contained therein. It is believed that the extended shelf-life is due to a reduced or eliminated diffusion of adhesive monomer, and monomer vapor, through the container due to the stabilizing effects of the incorporated antioxidant.

In embodiments, the containers of the present invention comprise an incorporated antioxidant stabilizer, such as a vitamin E antioxidant, derivatives thereof, or other suitable antioxidants including but not limited to those listed above, present on an internal surface of the container, preferably on each surface that is to contact a liquid or vapor composition comprising a 1,1-disubstituted ethylene monomer, or even on all surfaces of the container.

Containers of the present invention provide extended shelf-lives for 1,1-disubstituted ethylene monomer compositions, such as α-cyanoacrylate monomer compositions comprising α-cyanoacrylate monomers with lower and/or higher alkyl chain lengths. The containers of the present invention also provide extended shelf-lives for such monomer compositions that include no stabilizers, or only a sufficient amount of stabilizer to prevent premature polymerization of the monomeric material inside the lumen of the container. The containers can contain these monomer compositions for extended periods of time without showing visual evidence of container failure, such as cracking.

An indication of premature polymerization in 1,1-disubstituted ethylene monomer compositions, such as α-cyanoacrylate monomer compositions in particular, is an increase in viscosity of the composition over time. That is, as the composition polymerizes, the viscosity of the composition increases. If the viscosity becomes too high, i.e., too much premature polymerization has occurred, the composition becomes unsuitable for its intended use or becomes very difficult to apply. Thus, while some polymerization or thickening of the composition may occur, such as can be measured by changes in viscosity of the composition, such change is not so extensive as to destroy or significantly impair the usefulness of the composition. However, the present invention, by providing an antioxidant in the bulk material of the container, on the monomer-contacting surfaces of the container, or in the composition stored in the container decreases or prevents the premature polymerization of the composition, and thereby provides better control over the viscosity of the composition.

Suitable polymer materials for use in forming the container of the present invention include such polymeric materials, preferably amenable to incorporation of the antioxidant, that are suitable for fabrication of containers. Polymeric materials suitable for the container of the present invention include, but are not limited to, polyolefins and engineered resins.

Suitable polyolefins include, but are not limited to, polyethylene (PE), such as high-density polyethylene (HDPE), medium-density polyethylene; low-density polyethylene (LDPE), cross-linked high-density polyethylene (XLPE), linear low-density polyethylene (LLDPE), ultra low-density polyethylene, and very low-density polyethylene; polycarbonate (PC); polypropylene (PP); polypropylene copolymer (PPCO); polyallomer (PA); polymethylpentene (PMP or TPX); polyketone (PK); polyethylene terephthalates (PET), including polyethylene terephthalate G copolymer (PETG) and oriented PET; polystyrene (PS); polyvinylchloride (PVC); naphthalate; polybutylene terephthalate; thermoplastic elastomer (TPE); mixtures thereof; and the like. Exemplary densities of the above polyethylenes are as follows: LDPE—0.910–0.925 g/cm$^3$; medium-density polyethylene—0.926–0.940 g/cm$^3$; HDPE—0.941–0.965 g/cm$^3$. Other densities can be determined by the ordinary artisan by referencing ASTM D 1248 (1989).

Containers of the present invention can comprise engineered resins. Exemplary engineered resins include, but are not limited to, polyamide, such as nylon; polyphenylene oxides (PPO); polysulfone (PSF); mixtures thereof; and the like. In embodiments, the containers of the present invention can comprise mixtures of the above polyolefins, and/or engineered resins, so long as the resultant mixture is amenable to the incorporation of antioxidants.

Preferred containers of the present invention comprise polyethylene, which can be halogenated or non-halogenated, or functionalized or non-functionalized. In particular, various functional groups can be used to provide a barrier layer to decrease permeation of components of the monomer composition, and to provide an increased stabilizing effect to the monomer composition, thereby increasing the shelf-life of the container and composition. Suitable functional groups include, but are not limited to, $SO_3H$, $CO_2H$, $CONR_2$, COX, $CO_2R$, $SO_2X$, $SO_2NH_2$, $SO_2NR_2$, and mixtures thereof, where R represents a substituted or unsubstituted organic radical and X represents a halogen. A more detailed discussion of suitable functionalized containers according to the present invention is disclosed in U.S. Ser. No. 09/430,289, filed on Oct. 29, 1999, the entire disclosure of which is incorporated herein by reference. In embodiments, the preferred polymer comprises LDPE, LLDPE, HDPE, XLPE (cross-linked polyethylene) or PET, more preferably LDPE, LLDPE, HDPE, or PET, and most preferably, LLDPE, HDPE, or PET.

According to the present invention, the container can be any suitable container used to contain a polymerizable monomeric adhesive composition. Thus, the container can be formed out of any suitable material, and in any shape, size and/or construction, as desired. Suitable container constructions are disclosed, for example, in the above-referenced co-pending U.S. patent application Ser. No. 09/430,289, the entire disclosure of which is incorporated herein by reference. The only constraint is that in embodiments of the present invention wherein a storage container is stabilized by the incorporation of an antioxidant stabilizer, the container must be suitable for incorporating the stabilizer in the bulk material of the container or upon the monomer-contacting surfaces thereof, either during manufacture of the container or by a subsequent treatment with the antioxidant.

The antioxidant stabilizer may be integral with the container matrix or may be present in a laminate layer, preferably with a suitable polymeric material, on the container matrix. In embodiments where the antioxidant stabilizer is formed as a laminate over another material, the other material can be any other material suitable for forming the container, but is preferably also a polymeric material. Where the other material is a polymeric material, it can be any suitable polymeric material, including any of the above-described polyolefins and/or engineered resins. In embodiments where the antioxidant stabilizer is integral with the container matrix, the antioxidant stabilizer may be incorporated during a fabrication process conducted using a suitable polymeric material. Any of the various fabrication techniques known to the skilled artisan can be used. Included among these techniques are blow molding, injection molding and reaction-injection molding.

Also, although containers having various shapes and sizes may be suitable, in embodiments, the container is preferably sized so that the total volume is less than ten milliliters or less than one milliliter.

In embodiments, the method of the present invention further comprises sterilizing the 1,1-disubstituted ethylene monomer composition and/or its packaging, either prior to, or subsequent to, dispensing into the container. Suitable sterilization methods according to the present invention are disclosed in U.S. patent application Ser. No. 09/374,207 filed Aug. 12, 1999, the entire disclosure of which is incorporated herein by reference.

Sterilization of the monomer composition and/or its packaging can be accomplished by techniques known to one of ordinary skill in the art, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, gamma irradiation, electron beam irradiation, and microwave irradiation. A preferred method is electron beam irradiation, as described in U.S. patent application Ser. No. 09/025,472, filed on Feb. 18, 1998, the entire disclosure of which is incorporated herein by reference, as well as gamma irradiation. The composition must show low levels of toxicity to living tissue during its useful life. In preferred embodiments of the present invention, the composition is sterilized to provide a Sterility Assurance Level (SAL) of at least $10^{-3}$. In embodiments, the Sterility Assurance Level may be at least $10^{-4}$, or may be at least $10^{-5}$, or may be at least $10^{-6}$.

According to the invention, the combination of at least one antioxidant stabilizer provides sufficient inhibition of polymerization of the monomer (i.e., stabilization of the composition) that sterility can be achieved without the unacceptable levels of polymerization or increases in cure rate due to over-stabilization that result from methods disclosed in the prior art. For example, sterilized compositions according to embodiments of the present invention show an increase in viscosity of no more than 300%, and preferably less 150%, as a result of sterilization. Viscosity levels can be determined by known techniques. For example, viscosity can be determined at room temperature (approximately 21–25° C.) using a Brookfield Cone-Plate Viscometer. The instrument is standardized using a Viscosity Reference Standard in the same range as the sample to be tested. Each sample is measured three times, and an average value determined and recorded.

Thus, the present invention provides a method of manufacturing a container that provides an extended shelf-life for 1,1-disubstituted ethylene monomer compositions, as well as a container holding a 1,1-disubstituted ethylene monomer composition. The container can contain the 1,1-disubstituted ethylene monomer composition for extended periods of time before visual indications of failure, such as cracking of the container, are detectable. In embodiments, the period of time the container can contain the monomer composition is at least one or two years. Preferably, the length of time is at least 30 months, more preferably at least 36 months or 48 months.

As described above, the containers of the present invention also provide extended shelf-lives for such monomer compositions that include no stabilizers, or only a sufficient amount of stabilizer to prevent premature polymerization of the monomeric material inside the lumen of the container. The containers can contain these monomer compositions for extended periods of time without showing visual evidence of container failure, such as swelling, cracking, or blooming. Accordingly, a further benefit of the present invention is that monomer compositions can be provided that have a lesser amount of stabilizer than would otherwise be needed if stored in conventional containers, while having the same or equivalent degree of stabilization.

For example, as described above, acidic stabilizers are generally incorporated into a monomeric adhesive formulation in an amount of 10 to 300 ppm (wt/wt). However, in embodiments of the present invention, the amount of stabilizer added can be reduced or eliminated. Thus, for example, the amount of stabilizer can be reduced to an amount of about 90% or less, such as 80% or 70% or less, or 60% or 50% or less, or 40% or 30% or less, of the amount that would otherwise be needed if stored in conventional containers, while still having the same or equivalent degree of stabilization. In other embodiments, the amount of stabilizer can be reduced to 20% or even 10% or less, of the amount that would otherwise be needed if stored in conventional containers, while still providing the same or equivalent degree of stabilization. In still other embodiments, it is possible to omit additional stabilizers altogether, whereby the stabilizing effect is provided entirely by the containers of the present invention.

Advantages provided by antioxidant enriched containers are also seen when containers are designed for repeated use. Historically, it has been difficult to design containers for repeated dispensing of α-cyanoacrylate compositions due to the reactivity of the α-cyanoacrylate upon exposure to air. Typically, upon exposure to moisture in the air, the α-cyanoacrylate adhesive begins to polymerize. When α-cyanoacrylate monomer comes in contact with the threads of the bottle used to contain it, for example, the bottle tends to become permanently sealed upon replacement of the cap. However, it is believed that the containers of the present invention do not show this unwanted permanent sealing characteristic because the antioxidant stabilizer that is present in the container matrix and/or in the composition within the container inhibits polymerization of monomer present on the threads of the bottle/cap.

In embodiments of the present invention, the container is made, with incorporated antioxidant stabilizer, and filled with a 1,1-disubstituted ethylene monomer in a continuous process that can be fully automated. This fully automated process can be performed aseptically, allowing the manufacture of a sterile, sealed container of adhesive that can be used in both industrial and medical applications. Alternatively, in embodiments of the present invention, the container preferably is made with incorporated antioxidant stabilizer, filled with a 1,1-disubstituted ethylene monomer and then sterilized after being filled with monomer.

Preferred monomer compositions of the present invention, and polymers formed therefrom, are useful as tissue adhesives, sealants for preventing bleeding or for covering open wounds, and in other absorbable and non-absorbable biomedical applications. They find uses in, for example, apposing surgically incised or traumatically lacerated tissues; retarding blood flow from wounds; drug delivery; dressing burns; dressing skin or other superficial or surface wounds (such as abrasions, chaffed or raw skin, ulceration and/or stomatitis); hernia repair, meniscus repair; and aiding repair and re-growth of living tissue. Compositions of the present invention, and polymers formed therefrom, are also useful in industrial and home applications, for example in bonding rubbers, plastics, wood, composites, fabrics, and other natural and synthetic materials.

The monomer (including prepolymeric) adhesive composition may include one or more polymerizable monomers. Preferred monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers are disclosed in, for example, U.S. Pat. Nos. 5,328,687 and 5,928,611 to Leung et al., U.S. patent application Ser. No. 09/430,177, filed on Oct. 29, 1999, and U.S. patent application Ser. No. 09/471,392 filed Dec. 23, 1999, which are hereby incorporated in their entirety by reference herein. Preferred monomers include 1,1-disubstituted ethylene monomers, such as α-cyanoacrylates including, but not limited to, alkyl α-cyanoacrylates having an alkyl chain length of from about 1 to about 20 carbon atoms or more, preferably from about 3 to about 8 carbon atoms.

The α-cyanoacrylates of the present invention can be prepared according to several methods known in the art. U.S. Pat. Nos. 2,721,858, 3,254,111, 3,995,641, and 4,364,876, each of which is hereby incorporated in its entirety by reference herein, disclose methods for preparing α-cyanoacrylates.

Preferred α-cyanoacrylate monomers used in this invention include methyl cyanoacrylate, ethyl cyanoacrylate, n-butyl cyanoacrylate, 2-octyl cyanoacrylate, methoxyethyl cyanoacrylate, ethoxyethyl cyanoacrylate, dodecyl cyanoacrylate, 2-ethylhexyl cyanoacrylate, butyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, hexyl cyanoacrylate, or dodecylcyanoacrylate.

Suitable cyanoacrylates for use in the present invention also include, but are not limited to, alkyl ester cyanoacrylate monomers such as those having the formula

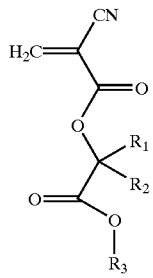

wherein $R_1$ and $R_2$ are, independently H, a straight, branched or cyclic alkyl, or are combined together in a cyclic alkyl group, and $R_3$ is a straight, branched or cyclic alkyl group. Preferably, $R_1$ is H or a $C_1$, $C_2$ or $C_3$ alkyl group, such as methyl or ethyl; $R_2$ is H or a $C_1$, $C_2$ or $C_3$ alkyl group, such as methyl or ethyl; and $R_3$ is a $C_1$–$C_{16}$ alkyl group, more preferably a $C_1$–$C_{10}$ alkyl group, such as methyl, ethyl, propyl, butyl, pentyl, hexyl, heptyl, octyl, nonyl or decyl, and even more preferably a $C_2$, $C_3$ or $C_4$ alkyl group. Such alkyl ester cyanoacrylates are disclosed in, for example, U.S. patent application Ser. No. 09/630,437, filed Aug. 2, 2000, the entire disclosure of which is incorporated herein by reference.

Examples of preferred alkyl ester cyanoacrylates include, but are not limited to, butyl lactoyl cyanoacrylate (BLCA), butyl glycoloyl cyanoacrylate (BGCA), ethyl lactoyl cyanoacrylate (ELCA), and ethyl glycoloyl cyanoacrylate (EGCA). BLCA may be represented by the above formula, wherein $R_1$ is H, $R_2$ is methyl and $R_3$ is butyl. BGCA may be represented by the above formula, wherein $R_1$ is H, $R_2$ is H and $R_3$ is butyl. ELCA may be represented by the above formula, wherein $R_1$ is H, $R_2$ is methyl and $R_3$ is ethyl. EGCA may be represented by the above formula, wherein $R_1$ is H, $R_2$ is H and $R_3$ is ethyl.

The composition may optionally also include at least one other plasticizing agent that assists in imparting flexibility to the polymer formed from the monomer. The plasticizing agent preferably contains little or no moisture and should not significantly affect the stability or polymerization of the monomer. Examples of suitable plasticizers include but are not limited to isopropyl myristate, isopropyl palimtate, tributyl citrate, acetyl tri-n-butyl citrate (ATBC), polymethylmethacrylate, polydimethylsiloxane, hexadimethylsilazane and others as listed in U.S. patent application Ser. No. 09/471,392 filed Dec. 23, 1999, the disclosure of which is incorporated in its entirety by reference herein.

The composition may also optionally include at least one thixotropic agent. Suitable thixotropic agents are known to the skilled artisan and include, but are not limited to, silica gels such as those treated with a silyl isocyanate, and optionally surface treated titanium dioxide. Examples of suitable thixotropic agents and thickeners are disclosed in, for example, U.S. Pat. No. 4,720,513, and U.S. patent application Ser. No. 09/374,207 filed Aug. 12, 1999, the disclosures of which are hereby incorporated in their entireties by reference herein.

The composition may optionally also include thickeners. Suitable thickeners may include poly (2-ethylhexy methacrylate), poly(2-ethylhexyl acrylate) and others as listed in U.S. patent application Ser. No. 09/472,392 filed Dec. 23, 1999, the disclosure of which is incorporated by reference herein in its entirety.

The composition may also optionally include at least one natural or synthetic rubber to impart impact resistance. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties by reference herein.

The composition may optionally also include one or more additional stabilizers, such as both at least one anionic vapor phase stabilizer and at least one anionic liquid phase stabilizer. These stabilizing agents may further inhibit premature polymerization. Suitable stabilizers may include those listed in U.S. patent application Ser. No. 09/471,392 filed on Dec. 23, 1999, the disclosure of which is incorporated by reference herein in its entirety.

The compositions may also include pH modifiers to control the rate of degradation of the resulting polymer, as disclosed in U.S. patent application Ser. No. 08/714,288, filed Sep. 18, 1996, the entire disclosure of which is hereby incorporated by reference herein in its entirety.

Compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites, etc. Additional examples of formaldehyde scavenger compounds useful in this invention and methods for their implementation can be found in U.S. Pat. Nos. 5,328,687, 5,514,371, 5,514,372, 5,575,997, 5,582,834 and 5,624,669, all to Leung et al., which are hereby incorporated herein by reference in their entireties.

To improve the cohesive strength of adhesives formed from the compositions of this invention, difunctional monomeric cross-linking agents may be added to the monomer compositions of this invention. Such crosslinking agents are known. U.S. Pat. No. 3,940,362 to Overhults, which is hereby incorporated herein in its entirety by reference, discloses exemplary cross-linking agents.

The compositions of this invention may further contain a fibrous reinforcement and colorants such as dyes, pigments, and pigment dyes. Examples of suitable fibrous reinforcements include PGA microfibrils, collagen microfibrils, and others as described in U.S. patent application Ser. No. 09/471,392 filed on Dec. 23, 1999, the disclosure of which is incorporated by reference herein in its entirety.

The polymerizable compositions useful in the present invention may also further contain one or more medicaments, preferably one or more non-antioxidant medicament. Suitable medicaments include, but are not limited to, antibiotics, antimicrobials, antiseptics, bacteriocins, bacteriostats, disinfectants, steroids, anesthetics, antifungal agents, anti-inflammatory agents, antibacterial agents, antiviral agents, antitumor agents, growth promoting substances, antioxidants, or mixtures thereof. Suitable specific medicaments are disclosed in, for example, U.S. patent application Ser. No. 09/430,177, filed Oct. 29, 1999, the entire disclosure of which is incorporated herein by reference.

The polymerizable compositions useful in the present invention may also further contain one or more preservatives. The preservatives may be present, for example, for prolonging the storage life of the composition and/or for destroying and/or usefully suppressing the growth or metabolism of a variety of microscopic or submicroscopic life forms, either in the composition itself, or in or on a substrate to which the composition may be applied. Suitable preservatives, and methods for selecting them and incorporating them into adhesive compositions, are disclosed in U.S. patent application Ser. No. 09/430,180, the entire disclosure of which is incorporated herein by reference.

In embodiments of the present invention, the composition and/or its applicator may contain materials such as a polymerization initiator, accelerator, rate-modifier, and/or cross-linking agent for initiating polymerization and/or cross-linking of the polymerizable monomer material. Suitable materials and applicators and packaging systems are disclosed in U.S. Pat. No. 5,928,611 and U.S. patent application Ser. Nos. 09/430,177, 09/430,176, 09/430,289, 09/430,290, and 09/430,180 filed Oct. 29, 1999; 09/343,914 filed Jun. 30, 1999; 09/385,030 filed Aug. 30, 1999; and 09/176,889 filed Oct. 22, 1998; the entire disclosures of which are incorporated herein by reference.

EXAMPLES

Example 1

Two cyanoacrylate monomer compositions are prepared using 2-octyl cyanoacrylate as the base monomer. The first composition is prepared as a control comprising no added antioxidant stabilizer. The second composition is prepared by adding chromanol in an amount of 5,000 ppm. Samples of each composition are placed into two chambers. The first chamber remains dark throughout the testing period, while the second chamber remains illuminated with fluorescent light throughout the testing period. The composition viscosity of each sample is tested at 3, 7 and 10 days to determine the stabilizing effects of the added chromanol on the composition upon exposure to fluorescent light. The results are presented in the Table below.

|  |  | Viscosity, cP | | |
| --- | --- | --- | --- | --- |
| Sample | Illumination | Day 3 | Day 7 | Day 10 |
| w/Chromanol | Dark | 6.7 | 6.5 | 6.6 |
|  | Fluorescent light | 6.7 | 9.6 | 6.7 |
| Control | Dark | 6.6 | 6.5 | 6.6 |
|  | Fluorescent light | 6.7 | 9.6 | 20 |

The results demonstrate that after 3 days the viscosity of both compositions remains nearly the same regardless of whether the compositions are exposed to light. At 7 days, both samples of the chromanol enriched composition maintain their viscosity; however, the sample of the control composition exposed to light exhibits more than a 40% increase in viscosity. Finally, at 10 days, the illuminated sample of the chromanol enriched composition exhibits only a slight increase in viscosity, whereas the illuminated sample of the control composition exhibits more than a 200% increase in viscosity.

Example 2

Two cyanoacrylate monomer compositions are prepared as in Example 1 above, using 2-octyl cyanoacrylate as the base monomer. The first composition is prepared as a control comprising no added antioxidant stabilizer. The second composition is prepared by adding pentamethylchromanol in an amount of 5,000 ppm. Samples of each composition are placed into a chamber that remains illuminated with fluorescent light throughout the testing period. The composition viscosity of each sample is tested at 3, 7, 10, 13 and 19 days to determine the stabilizing effects of the added pentamethylchromanol on the composition upon exposure to fluorescent light. The results are presented in the Table below.

|  | Viscosity, cP | | | | | |
| --- | --- | --- | --- | --- | --- | --- |
| Sample | Day 0 | Day 3 | Day 7 | Day 10 | Day 13 | Day 19 |
| w/Chromanol | 6.6 | 6.7 | 6.6 | 6.8 | 6.6 | 7 |
| Control | 6 | 6.7 | 9.7 | 20 | 23.8 | 93 |

Example 3

Two cyanoacrylate monomer compositions are prepared as in Example 2 above, using 2-octyl cyanoacrylate as the base monomer. However, prior to placing the samples into the chamber, the samples are heated to 160° C. for one hour and allowed to cool to room temperature. The samples are maintained in the chamber as above, and the composition viscosity of each sample is tested at 0, 4, 7, and 10 days to determine the stabilizing effects of the added pentamethylchromanol on the composition upon exposure to fluorescent light. The results are presented in the Table below.

|  | Viscosity, cP | | | |
| --- | --- | --- | --- | --- |
| Sample | Day 0 | Day 4 | Day 7 | Day 10 |
| w/Chromanol | 6.8 | 6.9 | 7 | 7 |
| Control | 6.9 | 10.9 | 20 | 36 |

Example 4

2-Octylcyanoacrylate (2-O CA) formulations are stabilized with radical stabilizers (BHA=butylated hydroxyanisole or chromanol=2,2,5,7,8-pentamethyl-6-chromanol) and stored in sealed glass ampoules. The glass ampoules are filled with 0.5 mL of the composition. The samples in sealed ampoules are subjected to gamma radiation or electron beam radiation sterilization, as shown in the tables below. The stability of the samples post radiation sterilization are monitored with time. The results are shown in the following tables.

| Formulation Stored in Glass ampoules | Viscosity Pre-ebeam (cps) | Post ebeam (cps), Samples exposed to 20 kilogray (kGy) | 6 days @ elevated temperature | 12 days at elevated temperature | 18 days at elevated temperature |
|---|---|---|---|---|---|
| Electron beam sterilization, 20 kGy | | | | | |
| 2-O CA (Control) | 6.1 | 9.7 | 39 | 113 | solid |
| 2-O CA + 5000 ppm BHA (comparative example) | 6.1 | 7.8 | 12 | 37 | 112 |
| 2-O CA + 5000 ppm pentamethyl chromanol | 6.1 | 6.5 | 8.7 | 15 | 52 |

| Formulation Stored in Glass ampoules | Viscosity Pre-ebeam (cps) | Post ebeam (cps), Samples exposed to 40 kilogray (kGy) | 6 days @ elevated temperature | 12 days at elevated temperature | 18 days at elevated temperature |
|---|---|---|---|---|---|
| Electron beam sterilization, 40 kGy | | | | | |
| 2-O CA (Control) | 6.1 | 15 | solid | solid | solid |
| 2-O CA + 5000 ppm BHA (comparative example) | 6.1 | 9.6 | solid | solid | solid |
| 2-O CA + 5000 ppm pentamethyl chromanol | 6.1 | 7.2 | 22 | 51 | 299 |

| Formulation Stored in Glass ampoules | Viscosity Pre-gamma (cps) | Post gamma (cps), Samples exposed to 20 kilogray (kGy) | 6 days @ elevated temperature | 12 days at elevated temperature |
|---|---|---|---|---|
| Gamma sterilization, 20 kGy | | | | |
| 2-O CA (Control) | 5.9 | 410 | solid | solid |
| 2-O CA + 5000 ppm BHA (comparative example) | 6 | 9.2 | 20 | 52 |
| 2-O CA + 5000 ppm pentamethyl chromanol | 6 | 6.3 | 8.6 | 26 |

| Formulation Stored in Glass ampoules | Viscosity Pre-gamma (cps) | Post gamma (cps), Samples exposed to 40 kilogray (kGy) | 6 days @ elevated temperature | 12 days at elevated temperature |
|---|---|---|---|---|
| Gamma sterilization, 40 kGy | | | | |
| 2-O CA (Control) | 5.9 | solid | solid | solid |
| 2-O CA + 5000 ppm BHA (comparative example) | 6 | 15 | solid | solid |
| 2-O CA + 5000 ppm pentamethyl chromanol | 6 | 7.0 | 11 | 48 |

Example 5

Following the procedures of Example 4, 2-Octylcyano-acrylate (2-O CA) formulations are stabilized with radical stabilizers (BHA=butylated hydroxyanisole or chromanol= 2,2,5,7,8-pentamethyl-6-chromanol) and stored in sealed glass ampoules or 3 cc fluorinated high-density polyethylene (FHDPE) bottles. The glass ampoules are filled with 0.5 mL of the composition; the FHDPE bottles are filled with 0.7 mL of the composition. The samples in sealed ampoules or 3 cc FHDPE bottles are subjected to gamma radiation or electron beam radiation sterilization, as shown in the tables below. The stability of the samples post radiation sterilization are monitored with time. The results are shown in the following tables.

Initial viscosity = 20 cP
Gamma sterilization, 25 kGy

| Formulation Stored in FHDPE bottles | Viscosity Pre-Gamma Radiation (cps) | Post Gamma Radiation (cps), Samples exposed to 25 kilogray (kGy) | 6 days @ elevated temperature (cps) | 12 days @ elevated temperature (cps) |
|---|---|---|---|---|
| 2-OCA (Control) | 20 | gel | solid | solid |
| 2-OCA + 5000 ppm BHA (Comparative Example) | 20 | 23 | 51 | solid |
| 2-OCA + 5000 ppm Pentamethylchromanol | 20 | 20 | 26 | thick |

Initial viscosity = 47 cP
Gamma sterilization, 25 kGy

| Formulation Stored in FHDPE bottles | Viscosity Pre-Gamma Radiation (cps) | Post Gamma Radiation (cps), Samples exposed to 25 kilogray (kGy) | 6 days @ elevated temperature (cps) | 12 days @ elevated temperature |
|---|---|---|---|---|
| 2-OCA (Control) | 47 | gel | solid | solid |
| 2-OCA + 5000 ppm BHA (Comparative Example) | 47 | 55 | 100 | 279 |
| 2-OCA + 5000 ppm Pentamethylchromanol | 47 | 44 | 49 | 93 |

Initial viscosity = 20 cP
Gamma sterilization, 25 kGy

| Formulation Stored in Glass ampoules | Viscosity Pre-Gamma Radiation (cps) | Post Gamma Radiation (cps), Samples exposed to 25 kilogray (kGy) | 6 days @ elevated temperature (cps) | 12 days @ elevated temperature (cps) |
|---|---|---|---|---|
| 2-OCA (Control) | 20 | Solid | solid | solid |
| 2-OCA + 5000 ppm BHA (Comparative Example) | 20 | 37 | thick | thick |
| 2-OCA + 5000 ppm Pentamethylchromanol | 20 | 21 | 37 | 113 |

Initial viscosity = 47 cP
Gamma sterilization, 25 kGy

| Formulation Stored in Glass ampoules | Viscosity Pre-Gamma Radiation (cps) | Post Gamma Radiation (cps), Samples exposed to 25 kilogray (kGy) | 6 days @ elevated temperature | 12 days @ elevated temperature |
|---|---|---|---|---|
| 2-OCA (Control) | 47 | 410 | solid | solid |
| 2-OCA + 5000 ppm BHA (Comparative Example) | 47 | 96 | thick | solid |
| 2-OCA + 5000 ppm Pentamethylchromanol | 47 | 45 | 78 | 169 |

| Formulation Stored in FHDPE bottles | Viscosity Pre-ebeam Radiation (cps) | Post ebeam (cps), Samples exposed to 25 kilogray (kGy) | 6 days @ elevated temperature | 12 days @ elevated temperature |
|---|---|---|---|---|
| Initial viscosity = 20 cP Electron beam sterilization, 25 kGy | | | | |
| 2-OCA (Control) | 20 | 29 | 43 | solid |
| 2-OCA + 5000 ppm BHA (Comparative Example) | 20 | 23 | 29 | 73 |
| 2-OCA + 5000 ppm Pentamethylchromanol | 20 | 20 | 24 | 25 |

-continued

| | Initial viscosity = 47 cP Electron beam sterilization, 25 kGy | | | |
|---|---|---|---|---|
| 2-OCA (Control) | 47 | 65 | 97 | solid |
| 2-OCA + 5000 ppm BHA (Comparative Example) | 47 | 51 | 67 | 146 |
| 2-OCA + 5000 ppm Pentamethylchromanol | 47 | 45 | 53 | 94 |

Initial viscosity = 20 cP
Electron beam sterilization, 25 kGy

| Formulation Stored in Glass ampoules | Viscosity Pre-ebeam Radiation (cps) | Post ebeam (cps), Samples exposed to 25 kilogray (kGy) | 6 days @ elevated temperature | 12 days @ elevated temperature |
|---|---|---|---|---|
| 2-OCA (Control) | 20 | 31 | 114 | 313 |
| 2-OCA + 5000 ppm BHA (Comparative Example) | 20 | 24 | 45 | 117 |
| 2-OCA + 5000 ppm Pentamethylchromanol | 20 | 21 | 27 | 55 |

Initial viscosity = 47 cP
Electron beam sterilization, 25 kGy

| Formulation Stored in Glass ampoules | Viscosity Pre-ebeam Radiation (cps) | Post ebeam Radiation (cps), Samples exposed to 25 kilogray (kGy) | 6 days @ elevated temperature | 12 days @ elevated temperature |
|---|---|---|---|---|
| 2-OCA (Control) | 47 | 72 | gel | solid |
| 2-OCA + 5000 ppm BHA (Comparative Example) | 47 | 54 | 81 | 200 |
| 2-OCA + 5000 ppm Pentamethylchromanol | 47 | 45 | 57 | 104 |

Example 6

Following the procedures of Examples 4 and 5, 2-Octylcyanoacrylate (2-O CA) formulations are stabilized with radical stabilizers (BHA=butylated hydroxyanisole or chromanol=2,2,5,7,8-pentamethyl-6-chromanol) and stored in large sealed glass ampoules filled with 1.2 mL of the composition. The samples in sealed ampoules are subjected to electron beam radiation sterilization, as shown in the tables below. The stability of the samples post radiation sterilization are monitored with time. The results are shown in the following tables.

Example 7

Following the general procedures above, n-butylcyanoacrylate (n-BuCA) adhesive formulations are stabilized with radical stabilizers (BHA=butylated hydroxyanisole or chromanol=2,2,5,7,8-pentamethyl-6-chromanol) and stored in sealed glass ampoules and or 3 cc fluorinated high-density polyethylene (FHDPE) bottles. The samples in sealed ampoules or 3 cc FHDPE bottles are subjected to gamma radiation or electron beam radiation sterilization and the stability of the samples post radiation sterilization are monitored with time. 0.5 mL filled ampoules and 1.2 mL filled

| Formulation Stored in Large ampoules | Viscosity Pre-ebeam Radiation (cps) | Post ebeam Radiation (cps), Samples exposed to 25 kilogray (kGy) | 6 days @ elevated temperature (cps) | 12 days @ elevated temperature (cps) |
|---|---|---|---|---|
| 2-OCA (Control) | 6.5 | 12 | 76 | Gel |
| 2-OCA + 5000 ppm BHA (Comparative Example) | 6.6 | 8.8 | 20 | 58 |
| 2-OCA + 5000 ppm Pentamethylchromanol | 6.6 | 7.8 | 12 | 32 |

FHDPE bottles were used for these experiments unless otherwise noted. The results are stated in the tables below:

Electron beam sterilization, 25 kGy

| Formulation Stored in FHDPE bottles | Viscosity Pre-ebeam Radiation (cps) | Post ebeam Radiation (cps), Samples exposed to 25 kilogray (kGy) | 6 days @ elevated temperature (cps) | 12 days @ elevated temperature (cps) |
| --- | --- | --- | --- | --- |
| n-BuCA (Control) | 3.1 | 12 | solid | solid |
| n-BuCA + 5000 ppm BHA (Comparative Example) | 3.1 | 5.1 | 23 | solid |
| n-BuCA + 5000 ppm Pentamethylchromanol | 3.1 | 5.1 | 13 | Thick gel |
| n-BuCA + 6108 ppm Pentamethylchromanol | 3.1 | 5.1 | 13 | Thick gel |

| Formulation Stored in Glass ampoules | Viscosity Pre-ebeam Radiation (cps) | Post ebeam Radiation (cps), Samples exposed to 25 kilogray (kGy) | 6 days @ elevated temperature (cps) | 12 days @ elevated temperature (cps) |
| --- | --- | --- | --- | --- |
| n-BuCA (Control) | 3.1 | 22 | solid | solid |
| n-BuCA + 5000 ppm BHA (Comparative Example) | 3.1 | 6.9 | 43 | solid |
| n-BuCA + 5000 ppm Pentamethylchromanol | 3.1 | 7.3 | 24 | Thick gel |
| n-BuCA + 6108 ppm Pentamethylchromanol | 3.1 | 6.9 | 21 | Thick gel |

Gamma beam sterilization, 25 kGy

| Formulation Stored in FHDPE bottles | Viscosity Pre-Gamma Radiation (cps) | Post Gamma Radiation (cps), Samples exposed to 25 kilogray (kGy) | 6 days @ elevated temperature (cps) | 12 days @ elevated temperature (cps) |
| --- | --- | --- | --- | --- |
| n-BuCA (Control) | 3.1 | solid | solid | solid |
| n-BuCA + 5000 ppm BHA (Comparative Example) | 3.1 | 4.7 | 710 | solid |
| n-BuCA + 5000 ppm Pentamethylchromanol | 3.1 | 4.0 | 13 | Thick gel |
| n-BuCA + 6108 ppm Pentamethylchromanol | 3.1 | 4.2 | 13 | Thick gel |

| Formulation Stored in Glass ampoules | Viscosity Pre-Gamma Radiation (cps) | Post Gamma Radiation (cps), Samples exposed to 25 kilogray (kGy) | 6 days @ elevated temperature (cps) | 12 days @ elevated temperature (cps) |
| --- | --- | --- | --- | --- |
| n-BuCA (Control) | 3.1 | solid | solid | solid |
| n-BuCA + 5000 ppm BHA (Comparative Example) | 3.1 | 5.7 | solid | solid |
| n-BuCA + 5000 ppm Pentamethylchromanol | 3.1 | 4.3 | 15 | Thick gel |
| n-BuCA + 6108 ppm Pentamethylchromanol | 3.1 | 4.4 | 17 | Thick gel |

While the invention has been described with reference to preferred embodiments, the invention is not limited to the specific examples given, and other embodiments and modifications can be made by those skilled in the art without departing from the spirit and the scope of the invention.

What is claimed is:

1. An adhesive composition comprising:
   a polymerizable 1,1-disubstituted ethylene monomer; and
   an antioxidant stabilizer selected from the group consisting of vitamin E and derivatives thereof in an amount of at least 0.1 percent by weight based on the monomer, vitamin K and derivatives thereof in an amount of at least 0.1 percent by weight based on the monomer, vitamin C and derivatives thereof in an amount of at least 0.1 percent by weight based on the monomer, pentamethyl chromanol, non-phenolic antioxidants, and pentamethylbenzofuranol.

2. The composition of claim 1, wherein said monomer is an α-cyanoacrylate.

3. The composition of claim 1, wherein said monomer is at least one member selected from the group consisting of methyl cyanoacrylate, ethyl cyanoacrylate, n-butyl cyanoacrylate, 2-octyl cyanoacrylate, methoxyethyl cyanoacrylate, ethoxyethyl cyanoacrylate, hexyl cyanoacrylate, dodecyl cyanoacrylate, butyl lactoyl cyanoacrylate, butyl glycoloyl cyanoacrylate, ethyl lactoyl cyanoacrylate, and ethyl glycoloyl cyanoacrylate.

4. The composition of claim 1, wherein said antioxidant stabilizer is a vitamin E antioxidant.

5. The composition of claim 4, wherein the antioxidant stabilizer is selected from the group consisting of alpha-tocopherol, beta-tocopherol, gamma-tocopherol, and delta-tocopherol.

6. The composition of claim 1, wherein said antioxidant stabilizer is pentamethyl chromanol.

7. The composition of claim 6, wherein the pentamethyl chromanol is 2,2,5,7,8-pentamethyl-6-chromanol.

8. The composition of claim 6, wherein the pentamethyl chromanol is present in an amount of at least 0.4 percent by weight based on the monomer.

9. The composition of claim 1, wherein said antioxidant stabilizer is a non-phenolic antioxidant.

10. The composition of claim 9, wherein said antioxidant stabilizer is selected from the group consisting of chromanols, benzopyranols, and benzofuranols.

11. The composition of claim 1, wherein said antioxidant stabilizer is a vitamin K or a derivative thereof.

12. The composition of claim 11, wherein said antioxidant stabilizer is vitamin $K_1$ chromanol.

13. The composition of claim 11, wherein said antioxidant stabilizer is vitamin $K_1$ chromenol.

14. The composition of claim 1, wherein said antioxidant stabilizer is vitamin C.

15. The composition of claim 1, wherein said antioxidant stabilizer is pentamethylbenzofuranol.

16. The composition of claim 1, wherein said antioxidant stabilizer is present in said composition in a concentration of at least 0.3% by weight.

17. The composition of claim 1, wherein said antioxidant stabilizer is present in said composition in a concentration of at least about 0.4 to about 2.0% by weight.

18. The composition of claim 1, wherein said composition has a Sterility Assurance Level of not better than $10^{-3}$.

19. The composition of claim 1, wherein said composition is sterilized to a Sterility Assurance Level of at least $10^{-3}$.

20. The composition of claim 1, further comprising a non-antioxidant medicament.

21. The composition of claim 1, further comprising a plasticizer.

22. A sterilized adhesive composition comprising:
a polymerizable 1,1-disubstituted ethylene monomer; and
an antioxidant stabilizer selected from the group consisting of vitamin E and derivatives thereof, vitamin K and derivatives thereof, vitamin C and derivatives thereof, pentamethyl chromanol, non-phenolic antioxidants, octyl gallate, and pentamethylbenzofuranol,
wherein the adhesive composition has a Sterility Assurance Level of at least $10^{-3}$.

23. The composition of claim 22, wherein said monomer is an α-cyanoacrylate.

24. The composition of claim 22, wherein said monomer is at least one member selected from the group consisting of methyl cyanoacrylate, ethyl cyanoacrylate, n-butyl cyanoacrylate, 2-octyl cyanoacrylate, methoxyethyl cyanoacrylate, ethoxyethyl cyanoacrylate, hexyl cyanoacrylate, dodecyl cyanoacrylate, butyl lactoyl cyanoacrylate, butyl glycoloyl cyanoacrylate, ethyl lactoyl cyanoacrylate, and ethyl glycoloyl cyanoacrylate.

25. The composition of claim 22, wherein said antioxidant stabilizer is a vitamin E antioxidant.

26. The composition of claim 25, wherein the antioxidant stabilizer is selected from the group consisting of alpha-tocopherol, beta-tocopherol, gamma-tocopherol, and delta-tocopherol.

27. The composition of claim 22, wherein said antioxidant stabilizer is pentamethyl chromanol.

28. The composition of claim 22, wherein the pentamethyl chromanol is 2,2,5,7,8-pentamethyl-6-chromanol.

29. The composition of claim 27, wherein the pentamethyl chromanol is present in an amount of at least 0.4 percent by weight based on the monomer.

30. The composition of claim 22, wherein said antioxidant stabilizer is a non-phenolic antioxidant.

31. The composition of claim 22, wherein said antioxidant stabilizer is a vitamin K or a derivative thereof.

32. The composition of claim 22, wherein said antioxidant stabilizer is vitamin C.

33. The composition of claim 22, wherein said antioxidant stabilizer is octyl gallate.

34. The composition of claim 22, wherein said antioxidant stabilizer is pentamethylbenzofuranol.

35. The composition of claim 22, wherein said antioxidant stabilizer is present in an amount sufficient to stabilize said composition during sterilization.

36. The composition of claim 22, wherein said antioxidant stabilizer is present in an amount sufficient to stabilize said composition during and subsequent to sterilization.

37. The composition of claim 22, wherein said antioxidant stabilizer is present in said composition in a concentration of at least 0.3% by weight.

38. The composition of claim 22, wherein said antioxidant stabilizer is present in said composition in a concentration of at least about 0.4 to about 2.0% by weight.

39. The composition of claim 22, further comprising a non-antioxidant medicament.

40. A method of making the adhesive composition of claim 1, comprising combining the polymerizable 1,1-disubstituted ethylene monomer and the antioxidant stabilizer.

41. A method of making the adhesive composition of claim 22, comprising combining the polymerizable 1,1-disubstituted ethylene monomer and the antioxidant stabilizer to form a mixture, and sterilizing the mixture.

42. The method of claim 41, wherein an amount of said antioxidant stabilizer is at least 0.3% by weight of the total composition.

43. A method of making a sterile polymerizable 1,1-disubstituted monomer adhesive composition comprising:
dispensing the polymerizable 1,1-disubstituted monomer adhesive composition of claim 1 into a container;
sealing said container; and
sterilizing the composition in the container.

44. A method of making a sterile polymerizable 1,1-disubstituted monomer adhesive composition comprising:
dispensing a polymerizable 1,1-disubstituted monomer adhesive composition into a container;
sealing said container; and
sterilizing the composition in the container to a Sterility Assurance Level of at least $10^{-3}$,
wherein said polymerizable 1,1-disubstituted monomer composition comprises:
at least one polymerizable 1,1-disubstituted ethylene monomer; and
an antioxidant stabilizer selected from the group consisting of vitamin E and derivatives thereof, vitamin K and derivatives thereof, vitamin C and derivatives thereof, pentamethyl chromanol, non-phenolic antioxidants, and pentamethylbenzofuranol.

45. The method of claim 44, wherein said sterilizing is by dry heat, gamma irradiation, electron beam irradiation, or microwave irradiation.

46. The method of claim 44, wherein said sterilizing is by electron beam irradiation.

47. The method of claim 44, wherein said sterilizing is by gamma irradiation.

48. The method of claim 44, wherein the sterilized composition has a viscosity less than 150% of a viscosity of said composition prior to sterilizing.

49. The method of claim 44, wherein said antioxidant stabilizer is a vitamin E antioxidant.

50. The method of claim 49, wherein the antioxidant stabilizer is selected from the group consisting of alpha-tocopherol, beta-tocopherol, gamma-tocopherol, and delta-tocopherol.

51. The method of claim 44, wherein said antioxidant stabilizer is pentamethyl chromanol.

52. The method of claim 51, wherein the pentamethyl chromanol is 2,2,5,7,8-pentamethyl-6-chromanol.

53. The method of claim 51, wherein said antioxidant stabilizer is a non-phenolic antioxidant.

54. The method of claim 44, wherein said antioxidant stabilizer is a vitamin K or a derivative thereof.

55. The method of claim 44, wherein said antioxidant stabilizer is ascorbic acid.

56. The method of claim 44, wherein said antioxidant stabilizer is octyl gallate.

57. The method of claim 44, wherein said antioxidant stabilizer is pentamethylbenzofuranol.

58. The method of claim 44, wherein said antioxidant stabilizer is present in an amount of at least 0.3 percent by weight based on the monomer.

59. The method of claim 44, wherein said composition has a total volume in said container of less than 10 milliliters.

60. A sterile composition made by the method of claim 44.

61. A polymerized film made by polymerizing the composition of claim 1.

62. A polymerized film made by polymerizing the composition of claim 22.

63. A method of making an adhesive composition comprising:

combining at least one polymerizable 1,1-disubstituted ethylene monomer, at least one antioxidant stabilizer, and at least one non-antioxidant medicament, wherein said at least one antioxidant stabilizer is selected from the group consisting of vitamin E and derivatives thereof, vitamin K and derivatives thereof, vitamin C and derivatives thereof, pentamethyl chromanol, non-phenolic antioxidants, and pentamethylbenzofuranol.

64. The method of claim 63, wherein said antioxidant stabilizer is a vitamin E antioxidant.

65. The method of claim 64, wherein said antioxidant stabilizer is a member selected from the group consisting of alpha-tocopherol, beta-tocopherol, gamma-tocopherol, and delta-tocopherol.

66. The method of claim 63, wherein said antioxidant stabilizer is a pentamethyl chromanol.

67. The method of claim 63, wherein said antioxidant stabilizer is a non-phenolic antioxidant.

68. The method of claim 63, wherein said antioxidant stabilizer is a vitamin K or a derivative thereof.

69. The method of claim 63, wherein said antioxidant stabilizer is vitamin C.

70. The method of claim 63, wherein said antioxidant stabilizer is pentamethylbenzofuranol.

71. The method of claim 63, further comprising:

dispensing the composition into a container;

sealing said container; and sterilizing the composition in the container.

72. A sterile composition made by the method of claim 71.

73. A method of treating tissue comprising:

applying the composition of claim 1 to tissue; and allowing the monomer to polymerize to form a polymer film.

74. The method of claim 73, wherein said antioxidant stabilizer is present in said polymer film in an amount effective to promote wound healing.

75. A method of treating tissue comprising:

applying the composition of claim 22 to tissue; and allowing the monomer to polymerize to form a polymer film.

76. The method of claim 75, wherein said antioxidant stabilizer is present in said polymer film in an amount effective to promote wound healing.

* * * * *